United States Patent [19]

Tsuru et al.

[11] Patent Number: 5,164,186
[45] Date of Patent: Nov. 17, 1992

[54] DRUG-RELEASER

[75] Inventors: Sumiaki Tsuru, Tokyo; Ichiro Masuno, Fukuoka, both of Japan

[73] Assignee: Kabushikigaisha ARS Japan, Tokyo, Japan

[21] Appl. No.: 617,376

[22] Filed: Nov. 21, 1990

Related U.S. Application Data

[62] Division of Ser. No. 257,841, Oct. 14, 1988, abandoned.

[51] Int. Cl.⁵ .............................................. A61F 13/00
[52] U.S. Cl. .................................... 424/422; 424/423
[58] Field of Search ................ 424/422, 484, 485, 487

[56] References Cited

U.S. PATENT DOCUMENTS

| | | | |
|---|---|---|---|
| 4,322,398 | 3/1982 | Reiner et al. | 424/484 |
| 4,610,692 | 9/1986 | Eitenmuller et al. | 424/423 |
| 4,747,845 | 5/1988 | Korol | 424/487 |

Primary Examiner—Thurman K. Page
Assistant Examiner—Leon R. Horne
Attorney, Agent, or Firm—Birch, Stewart, Kolasch & Birch

[57] ABSTRACT

Disclosed is a drug-releaser comprising a porous body of biocompatibility filled with a medicine. Specifically, such porous body is made of baked calcium phosphate, 2-hydroxyethylmethacrylate, chitin, chitosan or their delivatives. Implantation or artery-injection of such drug-releaser causes a discernible curing effect on affected parts of the living body without causing any irritativeness. The steady release of the medicine from HAP particles to affected parts and the blockade of surrounding capillary vessels leading to such affected parts causes a remarkable tumor inhibitory effect.

5 Claims, 5 Drawing Sheets

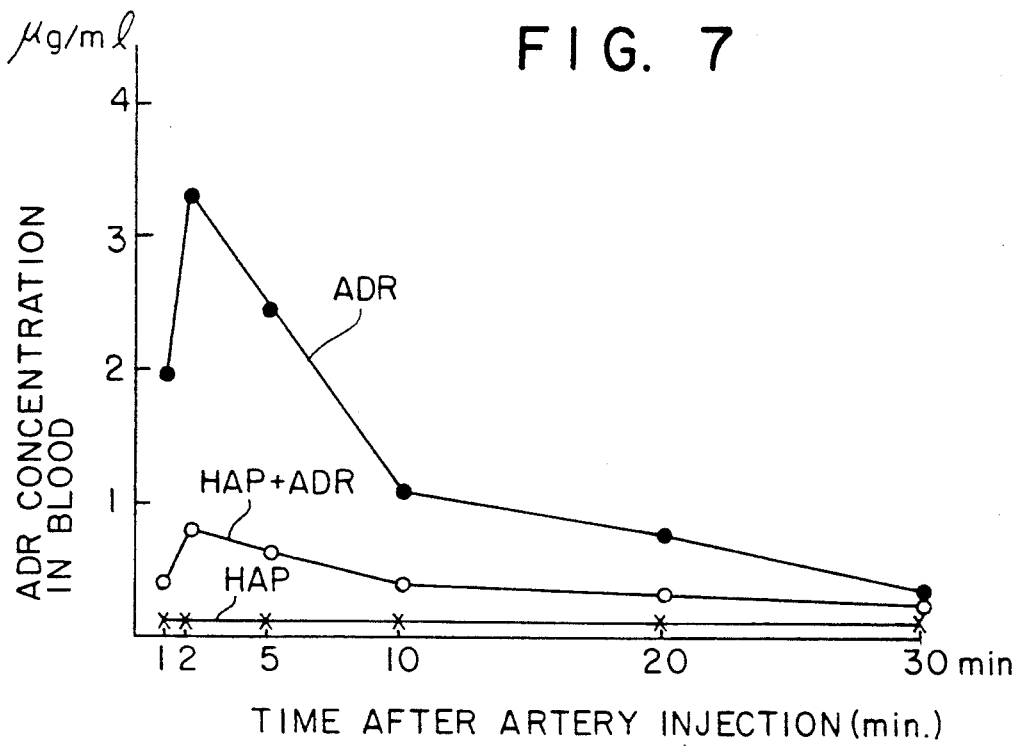
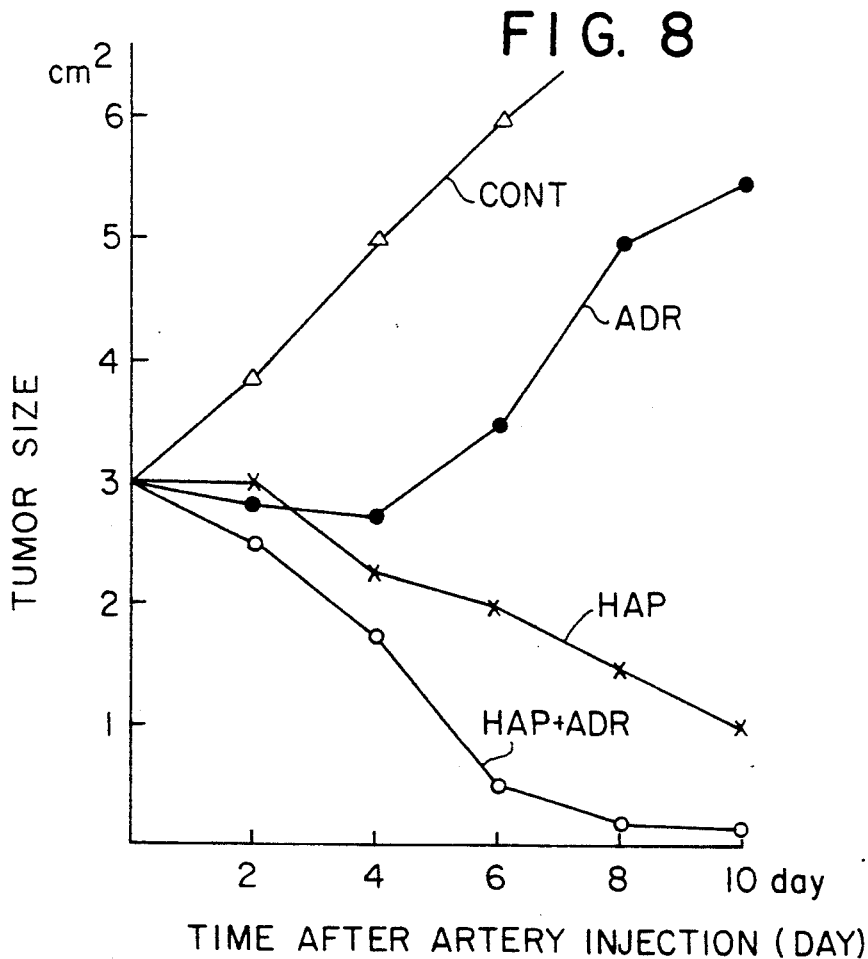

DRUG-RELEASER

This application is a divisional of application Ser. No. 07/257,841 filed on Oct. 14, 1988 now abandoned.

BACKGROUND OF THE INVENTION

1. Field of the Invention

The present invention relates to a drug-releaser which can carry a medicine to a localized affected part of a living body to permit the medicine to stay there for a relatively long time, thereby causing the medical effect long on the localized part of the living body.

2. Description of the Prior Art

In case that a medicine is applied to inflammation or tumor, the curing effect will depend on how long it can stay at that localized affected area. Generally speaking, the living body has a tendency to purge a medicine as a foreign substance from the body in the possible shortest time. Just after putting a medicine in the living body, the circulating blood starts absorption of the medicine, and the medicine will be purged out of the living body after passing through the kidney or the liver.

In order to keep the curing effect long lasting, it is necessary to retain the medicine in the vicinity of affected area as long as possible to prevent the prompt purge of the medicine from the living body. In an attempt to meet such a need a variety of dosing methods and drug-releasing materials have been proposed and actually used.

As one example, a medicine is put in a selected blood vessel little by little at intervals, thereby keeping the concentration of medicine in the blood at a given constant value. As another example, a given volume of medicine contained in a liposome capsule is put in the living body through the mouth, and then the encapsulated medicine will be gradually absorbed in the intestinal wall while passing through the intestinal canals in ten-odd hours. These conventional dosing methods, however, cannot permit the medicine to stay in the vicinity of the affected areas of the living body, such as tumors, and therefore, the medicine cannot exercise its curing effect on the affected part to its maximum capability.

In view of the above, one object of the present invention is to provide a drug-releaser which is free from the defect of conventional dosing methods as described above, permitting the medicine to stay long enough to make full use of its curing effect on the affected area of the body.

SUMMARY OF THE INVENTION

To attain this object a drug-releaser according to the present invention comprises a porous body of biocompatibility filled with a medicine. This porous body may be embeded to be in direct contact with a selected affected part or in the vicinity of the selected affected part. A porous body may take the form of minute particle. Medicine-filled minute particles may be put in a selected blood vessel which leads to a selected affected part to be treated. The requirements of a drug-releaser according to the present invention are: first, it is non-immunogenic, nontoxic, or non-irritating but is biocompatible, and second, its porosity is large enough to hold a relatively large amount of medicine.

Materials to meet such requirements are:

(1) Inorganic matter: hydroxycalciumapatite(HAP), calcium-triphosphate(TCP) and other calcium phosphates;
(2) Organic matter: 2-hydroxyethylmethacrylate(HEMA) or polyvinylalcohol(PVA);
(3) Natural macromolecular matter: chitin or chitosan and chitosan delivatives;and
(4) Natural macromolecular matter: collagen and collagen delivatives These substances have a biocompatibility, and can be prepared to be porous. In fact, such porous particles weighing one gram can have total surface area ranging from 50 to 500 $m^2$ in their open pores, thus providing sufficient area in which as much medicine as required can be absorbed and held.

Specifically, the substances in group (1) can become porous by mixing with a blowing agent such as hydrogen peroxide, drying the resultant slurry like mixture and baking the dry mixture. The substances in groups (2), (3) and (4) can become porous by mixing evenly with certain mediums, and freezing the mixture to be dry.

HAP and TCP in group (1) have high-absorbing capabilities in a variety of chemically binding forms, for instance chelate bond, hydrogen bond and quadrapole interaction with respect to protein, sugar, proteoglycan and other macromolecular substances. Porous bodies of these substances are appropriate for the purpose of holding an increased amount of medicine such as polysaccharide (anticancer drug) in their open pores and carrying to affected parts of the living body.

As for HEMA, PVA, chitin chitosan, collagen and their derivatives: these substances in groups (2), (3) and (4) have hydrophilicity and hydrophobicity in balance on their surfaces. These characteristics along with electro static nature on their surfaces cause effective absorption of protein, dye and saccharide. Thus, porous bodies which are made of these materials, are appropriate for the purpose of holding and carrying an increased amount of medicine to affected parts of the living body.

BRIEF DESCRIPTION OF THE DRAWINGS

FIGS. 1 (B) to 3 (B), 5 (B) and 6 (B) are side views of the drug-releasers; and FIG. 4 (B) is a sectional view of the drug-releaser.

FIG. 7 shows how the ADR concentration in mouse blood varies with time in the chemical treatment using Adriamycin (ADR 1.5 mg/Kg).

FIG. 8 shows how the tumor size varies with time in the chemical treatment using Adriamycin (ADR 1.5 mg/Kg).

Figure 1A:
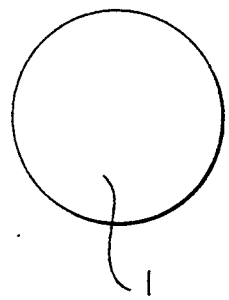
FIGS. 1 to 6 show different drug-releasers according to the present invention. Particularly, FIGS. 1 (A) to 6 (A) are plane views of the drug-releasers.
Figure 2A:
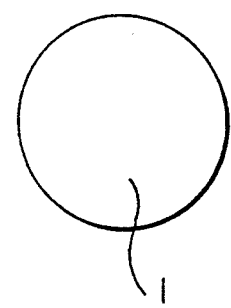
Figure 1B:
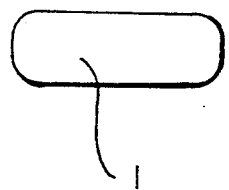

Some examples of porous bodies of the substances described above in groups (1), (2), (3) and (4) are shown in FIGS. 1 and 2.

A drug-releasing porous disk 1 of FIG. 1 is 1 millimeter thick and 5 millimeters across, and has open pores. The pore size ranges from 50 to 500 millimicrons.

First, the porous disk is subjected to sterilization, and the disk thus sterilized is soaked in a medicine solution. When surrounding pressure is decreased, air is replaced by medicine in every pore, and then the medicine is absorbed in the inner wall of the pore. Thus, a drug-releasing disk 1 results. When this disk is implanted in the vicinity of a tumor to be treated, the medicine will continuously apply its effect on the tumor for a relatively long period. Specifically, it ranges from several weeks to several months, depending on the size of the disk, the medicine absorbing-and-holding energy, and other factors.

Some medicines require the use of ligand, which has an effect to bond the medicine to the inner surface of each pore. The porous material of the drug-releasing disk has a very high biocompatibility, and therefore the disk can be held firmly by normal cells or by ingrowthes of intercellularmatrix in the living body. Then, the medicine will be released from every pore to pass through the cell membrane or intercellularmatrix, and arrive at the target cells. The medicine can have an inclination to target selected cells when combined with a monoclonal antibody to the selected cells.

Figure 2B:
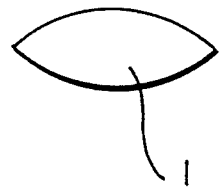
Figure 3A:
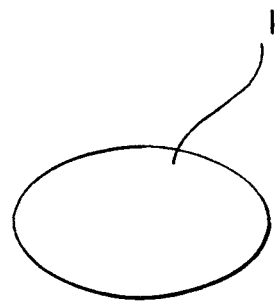
Figure 3B:
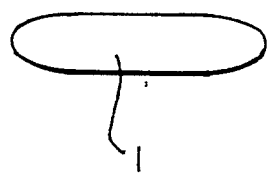

The disk 1 of FIG. 1 has a rounded circumferential edge or else it would hurt surrounding tissue. The disk can have a different shape in section as shown in FIG. 2B for the same reason. Also, an egg-shaped body 1 as shown in FIG. 3 may be used even more safely.

Figure 4A:
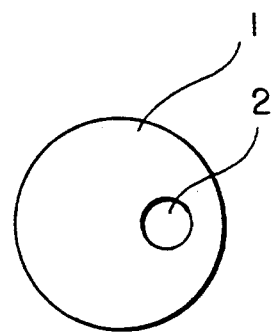
Figure 4B:
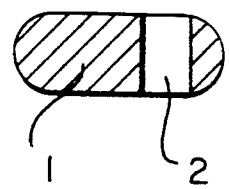
Figure 5A:
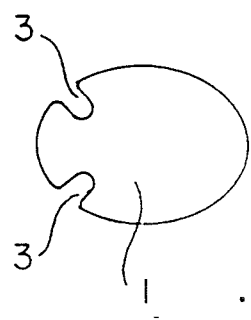
Figure 6A:
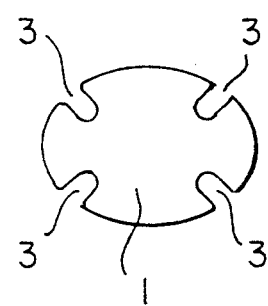
Figure 5B:
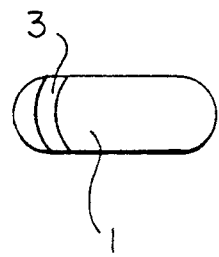
Figure 6B:
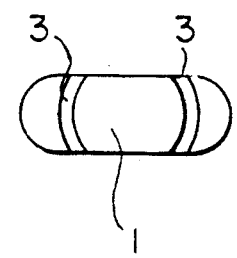

A thin body 1 of FIG. 4 has a small hole 2 for the purpose of facilitating the binding to tissue. Thin bodies of FIGS. 5 and 6 have reentracies 3 for the same purpose.

Different medicines can be carried by a single drug-releasing disk, thereby making full use of the composite curing effect on the affected parts of the living body. A plurality of drug-releasing disks may be implanted in the vicinity of a selected affected part, thereby causing composite curing effects on the same affected part.

All disks of FIGS. 1 to 6 are several to ten-odd millimeters across. Larger or smaller disks are difficult to be implanted at fixed places in the living body.

Next, some examples of making minute particles from drug-releasing material are given.

Calcined particles of hydroxycalciumapatite (HAP) or calcium phosphate such as calcium-triphosphate (TCP) may be used. These particles are 10 to 1000 millimicrons across. Particles whose size is below 10 millimicrons across, are easy to be transported by blood when injected in the artery, and therefore there is a fear of accumulation of particles in the kindney. Particles whose size is above 1000 millimicrons across, are difficult to be injected in the artery.

The P-to-C ratio in the composition of calcium phosphate is preferably equal to or larger than 1.0, but smaller than 2.0 ($1.0 \leq Ca/P < 2.0$). The Ca/P ratio out of the range will make the drug-releasing material easy to melt, lowering the capability of holding and steadily releasing the medicine for an extended period.

The temperature at which calcium phosphate is calcined, preferably ranges from 600 to 1350 degrees Centigrade. Calcination at a temperature below 600 degrees Centigrade is inadequate to form particles, and the calcined material has a poor capability of absorbing macrophage-like monocytes. The calcination at a temperature above 1350 degrees Centigrade will decompose apatite, and therefore no active ceramic material can result.

Assume that drug-releasing particles thus made are injected into an artery leading to a selected tumor such as cancer in the living body. The drug-releasing particles reach and stay at the cancer, causing long-lasting curing effect on the cancer, and at the same time, they may accumulate there to block capillary vessels leading to the cancer, thereby preventing the supply of nourishment to the cancer and hence the growth of the cancer.

Some examples of applying drug-releasing particles to experimental tumors and malignant tumors in human libers are given below:

EXAMPLES

The curing effect of drug-releasing particles was studied on MethA tumors which were grafted in the muscles of the rear right legs of some selected mice.

Calcium phosphate which was used, was hydroxycalciumapatite (pure apatite; HAP). Its particulars are: calcination temperature: 700 to 800 degrees Centigrade, stoichiometry Ca/P: 1.66..., and average particle size: 50 to 100 millimicrons.

When 2 weeks had passed after grafting tumor on the rear right legs of some selected mice, these mice were separated in two groups. Adriamycin (ADR 1.5 milligrams/kg) was injected in the common iliac arteries on the same side as MethA tumors were grafted in the first group of mice. Likewise, Apatite (HAP) particles filled with Adriamycin (ADR) were arteri-injected in the second group of mice. The ADR concentration was determined on each blood sample which was taken from the fundas venosus plexus of every mouse at intervals (HPLC method), and tumor inhibitory effect was checked.

The ADR concentrations in serum reached peak values 2 minutes after the artery injections in the first and second groups. The ADR concentration in the HAP+ADR artery-injected group was significantly low ($p<0.005$), compared with that in the ADR artery-injected group (See FIG. 7).

The ADR concentration in tumor was significantly high in the HAP+ADR artery-injected group ($p<0.001$): The HAP particles appeared to have functioned as micro-blockader, therby causing the tumor to hold an increased concentration of ADR (See Table 1).

No tumor inhibitory effect was found in the ADR artery-injected group (1.5 mg/kg), whereas a remarkable inhibitory effect was found in the HAP+ADR artery-injected group. A discernible tumor inhibitory effect was found in the HAP artery-injected group (See FIG. 8).

REFERENCE EXAMPLES

Selected were 15 patients whose liver cancer could not be treated by surgical operation.

The same calcium phosphate as used in the above examples, was used. Developing tumors were studied by angiography and CT according to the hepatoma dealing standard. Selected were 5 samples in 2 areas; 3 samples in 3 areas; and 7 samples in 4 areas and remote transpositions.

7 samples thus selected were block; 6 samples were tuberous; and 2 samples were infiltrative.

The HAP particles filled with ADR (20 to 50 milligrams) were used. The safety injection of HAP-ADR into the stomacduodenum artery was not assured, and therfore necessary injections were effected in the liver artery and selected arteries on the side of the liver. Only one treatment was effected.

The curing effect was checked in terms of reduction of the tumor area mainly with the aid of angiography, and also the ultrasonic diagonosis state was taken into consideration.

Figure 9:
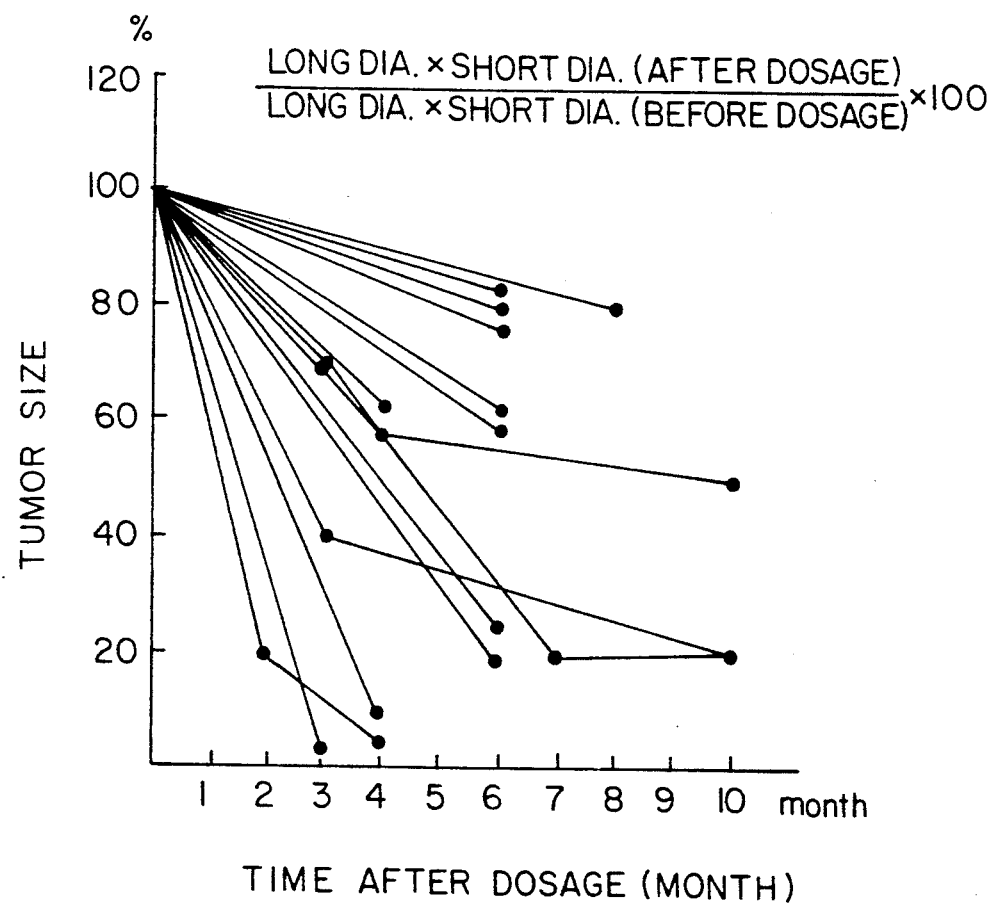
FIG. 9 shows how the tumor size varies with time in the chemical treatment of selected 15 patients.

7 examples showed tumor reduction of 50 or more percent(PR); 4 examples showed tumor reduction of 20 to 50 percent(MR); 4 examples showed tumor reduction of 25 or less percent (NC); and no examples showed tumor enlargement of 25 or more percent (PD). Briefly speaking, the curing effect which was equal to or greater than PR, was 47 percent, and that which was equal to or greater than MR, was 73 percent (See FIG. 9).

As is apparent from the above, only one artery-injection of baked particles of hydroxycalciumapatite or calcium-triphosphate caused a discernible curing effect on affected parts of the living body without causing any irritativeness. The steady release of the medicine from HAP particles to affected parts and the blockade of surrounding capillary vessels caused a remarkable tumor inhibitory effect.

TABLE 1

The ADR concentration in tumor one hour after the chemical blockade treatment using ADR (1.5 mg/kg)

| chemical treatment | ADR concentration ($\mu g/g$) |
| --- | --- |
| ADR alone | 4.8 |
| HAP + ADR blockade | 11.6 |

What is claimed is:

1. A method of treating a selected area of a body which comprises injecting an effective amount of a drug releasing composition which comprises
   (a) particles of baked calcium phosphate having an average particle size of from 10 to 1000 $\mu m$ and wherein the Ca/P ratio is greater than or equal to 1 and less than 2 and wherein the calcination temperature of said calcium phosphate is in the range of from 600° to 1350° C.; and
   (b) a medicine dispersed through said particles into an artery leading to said selected area of the body to be treated.

2. The method according to claim 1, wherein said selected area of the body to be treated is a tumor.

3. The method according to claim 1 wherein said baked calcium phosphate is hydroxycalciumapatite.

4. A method of treating a tumor in a selected area of the body which comprises injecting an anti-tumor effective amount of a polysaccharide anticancer active agent-releasing composition into an artery leading to said selected area of the body to be treated, said composition comprising:
   (a) particles of baked calcium phosphate having an average particle size of from 10 to 1,000 $\mu m$ and wherein the Ca/P ratio is greater than or equal to 1 and less than 2 and wherein the calcination temperature of said calcium phosphate is in the range of from 600° to 1350° C.; and
   (b) an anti-tumor effective amount of a polysaccharide anticancer active agent dispersed through said particle.

5. A method of treating a tumor in a selected area of the body which comprises injecting an adriamycin-releasing composition into an artery leading to said selected area of the body to be treated, said composition comprising:
   (a) particles of baked calcium phosphate having an average particle size of from 10 to 1,000 $\mu m$ and wherein the Ca/P ratio is greater than or equal to 1 and less than 2 and wherein the calcination temperature of said calcium phosphate is in the range of from 600° to 1350° C.; and
   (b) an anti-tumor effective amount of adriamycin dispersed through said particles.

* * * * *